(12) United States Patent
Otera

(10) Patent No.: US 10,337,988 B2
(45) Date of Patent: Jul. 2, 2019

(54) DEVICE FOR MEASURING MOISTURE IN A GAS

(75) Inventor: Fumiaki Otera, Kyoto (JP)

(73) Assignee: Shimadzu Co., Kyoto (JP)

( * ) Notice: Subject to any disclaimer, the term of this patent is extended or adjusted under 35 U.S.C. 154(b) by 511 days.

(21) Appl. No.: 13/488,125

(22) Filed: Jun. 4, 2012

(65) Prior Publication Data
US 2013/0319110 A1 Dec. 5, 2013

(51) Int. Cl.
| | |
|---|---|
| *G01N 21/81* | (2006.01) |
| *G01N 21/3504* | (2014.01) |
| *G01N 21/3554* | (2014.01) |
| *G01N 21/359* | (2014.01) |
| G01N 21/03 | (2006.01) |
| G01N 21/39 | (2006.01) |

(52) U.S. Cl.
CPC ........ *G01N 21/3504* (2013.01); *G01N 21/359* (2013.01); *G01N 21/3554* (2013.01); *G01N 21/031* (2013.01); *G01N 2021/399* (2013.01)

(58) Field of Classification Search
CPC ........ G01N 21/81; G01N 21/33; B60S 1/0822
USPC ..................................................... 73/335.01
See application file for complete search history.

(56) References Cited

U.S. PATENT DOCUMENTS

| | | | | |
|---|---|---|---|---|
| 4,847,512 A | * | 7/1989 | Seta | 250/575 |
| 6,164,817 A | * | 12/2000 | Trainer | 374/19 |
| 2004/0021078 A1 | * | 2/2004 | Hagler | G01J 3/1804 |
| | | | | 250/339.13 |

FOREIGN PATENT DOCUMENTS

| | | |
|---|---|---|
| JP | 05-099845 | 4/1993 |
| JP | 11-083665 | 3/1999 |
| JP | 2009192246 A * | 8/2009 |

* cited by examiner

*Primary Examiner* — Son T Le
*Assistant Examiner* — Alex T Devito
(74) *Attorney, Agent, or Firm* — Chris Mizumoto

(57) ABSTRACT

Modulation amplitude used for frequency modulation of laser light is set to a1 (<a2) (S1), and laser light is irradiated to a sample state in that state. When moisture concentration is calculated based on secondary harmonic synchronous detection signal that is obtained by synchronous detection of detection signal from transmitted light, the effects of interfering moisture in the optical chamber is ignored, and moisture concentration of the gas to be measured in the sample cell is obtained (S2). If, for example, a high vacuum is created inside the sample cell and the concentration becomes less than the detectable limit ("YES" in S3), the modulation amplitude is switched to a larger amount a2 (S4). By so doing, the detection sensitivity to interfering moisture in atmosphere at atmospheric pressure is increased, and the concentration of interfering moisture is calculated based on the secondary harmonic synchronous detection signal (S5).

7 Claims, 8 Drawing Sheets

DEVICE FOR MEASURING MOISTURE IN A GAS

TECHNICAL FIELD

The present invention relates to a moisture measurement device that uses absorption of laser light for measuring moisture concentration in a gas and, in particular, to a moisture measurement device that is well suited for measuring the concentration of minute amounts of moisture in a gas.

BACKGROUND ART

Methods known from the past for measuring moisture (water vapor) concentration in a gas include the crystal oscillation method and the electrostatic capacitance method. With the crystal oscillation method, a sensitive membrane that absorbs moisture that is present in a gas is adhered to a crystal oscillator and the change in frequency of the crystal oscillator is measured. With the electrostatic capacitance method, the change in electrostatic capacitance of a sensitive membrane is measured. However, these methods are not suited for the measurement of minute quantities of moisture and also suffer from poor stability of the measurements caused by a drop in measurement accuracy due to factors such as degradation of the sensitive membrane. A moisture measurement device that has been proposed in recent years for measuring moisture concentration in gas uses infrared absorption spectroscopy that is based on the absorption of laser light in the infrared region (see for example Patent Literature 1 and 2).

With this moisture measurement device, laser light having a predetermined wavelength is irradiated onto a sample cell in which gas to be measured is introduced and transmitted laser light is analyzed to determine moisture concentration from the amount of absorption by the moisture in the gas. Because the device is a non-contact type and the light reception unit that serves as the sensor does not contact the gas to be measured, the device, unlike previous devices that employ the crystal oscillation method or the electrostatic capacitance method, can be used for the measurement of moisture in corrosive gases. Furthermore, because moisture measurement can be performed quickly, the device is suited for purposes such as the continuous monitoring of moisture concentration in a flowing gas.

Among such infrared absorption spectroscopy that uses laser light, harmonic detection spectroscopy that uses secondary harmonics is particularly well known (see for example Non-Patent Literature 1). Non-Patent Literature 2 discloses a moisture measurement method that uses harmonic detection spectroscopy. The theory behind moisture measurement according to this literature is briefly explained next.

If vaporized moisture is present in air or nitrogen (gas to be measured) with a gas pressure of 1 atmosphere or more, the shape of the absorption property is represented by a Lorentz profile identified by equation (1) below.

Equation 1

$$I_0(v) - I(v) = \frac{1}{\pi} \frac{PcLS\gamma}{(v - v_0)^2 + \gamma^2} \tag{1}$$

Here, $I_0(v)$ represents the intensity of the incident light at frequency v, and $I(v)$ represents the intensity of the transmitted light at frequency v. P represents the gas pressure, c the volume concentration of water molecules, L the length of the optical path passing through the gas to be measured, and S the predetermined linear strength of absorption property, $\gamma$ the half-width of the absorption property, and $v_0$ the center frequency for the frequency modulation. Equation (2) below represents the absorption intensity $I(v_0)$ at the center frequency $v_0$.

Equation 2

$$I_0(v_0) - I(v_0) = \frac{1}{\pi} \frac{PcLS}{\gamma} \tag{2}$$

Infrared absorption by water molecules in very low total pressure regions (high vacuum regions where the total pressure of the gas to be measured is no more than 1 Torr) results in the width of the absorption property to be narrower than the width of the aforesaid Lorentz profile by a factor of several-fold to several dozen-fold. The width of the absorption property in said total pressure region is primarily determined by the Doppler effect. The width of the absorption property is represented by a Gaussian line shape expressed by equation (3) below.

Equation 3

$$I_0(v) - I(v) = \frac{1}{\gamma_{ED}\sqrt{\pi}} \frac{PcLS}{\exp\left(\frac{v - v_0}{\gamma_{ED}}\right)^2} \tag{3}$$

In equation (3), $\gamma_{ED}$ is referred to as the Doppler width and depends on the center frequency of the absorption frequency, molecular weight and temperature. Here, the absorption intensity $I(v_0)$ at center frequency $v_0$ is represented by equation (4) below.

Equation 4

$$I_0(v_0) - I(v_0) = \frac{PcLS}{\gamma_{ED}\sqrt{\pi}} \tag{4}$$

Under conditions of a high vacuum and at room temperature of approximately 25° C., with an absorption spectrum in a region of relatively strong absorption that allows the use of an ordinary near-infrared semiconductor laser, $\gamma_{ED}$ is approximately equal to 0.01 $cm^{-1}$. With water molecules that are present in air or nitrogen matrix at 1 atmospheric pressure, the general value of $\gamma$ is 0.1 $cm^{-1}$.

Performing harmonic detection requires modulation of the frequency of light that is irradiated onto the gas to be measured. Letting a represent the modulation amplitude of a sine wave signal for frequency modulation and w represent frequency, the frequency of light at time t is defined by equation (5) below.

Equation 5

$$v \bmod(t) = v + a \cdot \cos \omega t \tag{5}$$

With a second harmonic detection, signal components that correspond to twice the frequency or 2ω are extracted. The second harmonic detection signal at center frequency $v_0$ for water molecules that are present in air or nitrogen at 1 atmospheric pressure is defined by equation (6) below.

Equation 6

$$\text{signal}(v_0) \frac{2}{\pi} \frac{PcLS}{\gamma} \int_0^{\pi} \frac{\cos(2\theta)}{\left(\frac{a\cos\theta}{\gamma}\right)^2 + 1} d\theta \quad (6)$$

Similarly, the second harmonic detection signal at center frequency $v_0$ for water molecules in a vacuum atmosphere is defined by equation (7) below.

Equation 7

$$\text{signal}(v_0) \frac{2}{\sqrt{\pi}} \frac{PcLS}{\gamma_{ED}} \int_0^{\pi} \frac{\cos(2\theta)}{\exp\left(\frac{a\cos\theta}{\gamma_{ED}}\right)^2} d\theta \quad (7)$$

Non-Patent Literature 2 proves that signal ($v_0$) with the highest sensitivity is obtained when the modulation amplitude a is selected so that a/γ (or a/$\gamma_{ED}$)=2.2 in equations (6) and (7) above.

Even though the afore-described moisture measurement method that uses laser light has advantages over previous measurement methods, it also has the following problems. To explain, laser light passes through not just the gas to be measured but also space occupied by other than the gas to be measured. This results in the moisture (hereinafter "interfering moisture") derived from the atmosphere that is present in that space to act as background noise that affects the measurement results. To eliminate these effects, what is typically done is to supply a purge gas into the chamber that houses optical system elements such as laser light source and photodetectors to reduce the amount of interfering moisture.

However, because the interfering moisture exists in atmosphere in large quantities, even if the afore-described method is used, to guarantee that the interfering moisture is eliminated with certainty requires that the status of interfering moisture be continuously monitored. This is particularly so with equipment that is used in semiconductor manufacturing processes for monitoring and measuring moisture concentration in a gas for extended periods. With such equipment, it is important to maintain the dehumidifying capacity of purge gas that is supplied in large quantities at a constant level, and this requires measuring the amount of interfering moisture in the purge gas. However, methods or devices for easily measuring interfering moisture have not been proposed previously.

PRIOR ART LITERATURE

Patent Literature

Patent Literature 1: Unexamined Patent Application Publication No. Hei 05-99845
Patent Literature 2 Unexamined Patent Application Publication No. Hei 11-83665

Non-Patent Literature

Non-Patent Literature 1: C. R. Webster, "Infrared Laser Absorption: Theory and Applications in Laser Remote Chemical Analysis," Wiley, New York, 1988

Non-Patent Literature 2: G. V. H. Wilson, "Modulation Broadening of NMR and ESR Line Shapes," J. Appl. Phys., Vol. 34, No. 11, pp. 3276 (1963)

OVERVIEW OF THE INVENTION

Problems to be Solved by the Invention

The present invention was made in light of the afore-described problems, and it is the object of the present invention to provide a moisture measurement device that can accurately and easily monitor the amount of interfering moisture regardless of whether or not the interfering moisture is affecting the measurement system as background noise and also prevent the measurement system from entering an abnormal state.

Means for Solving the Problems

The present invention which was made to solve the afore-described problems is a device for measuring moisture in a gas, the device comprising:
a sample cell where gas to be measured is introduced;
a laser irradiation unit and a light reception unit disposed outside of the sample cell;
wherein laser light modulated using frequency f and emitted from the laser irradiation unit is detected by the light reception unit after passing through the gas to be measured in the sample cell;
the detection signal is synchronously detected using a frequency that is an integer-multiple of frequency f; and
concentration of moisture that is included in the gas to be measured is calculated based on the detection result; and further comprising:
a) a modulation amplitude setting means for switchably setting the modulation amplitude between at least two types; and
b) a moisture calculation means for calculating moisture concentration in the sample cell based on detection signal that is obtained when a relatively small modulation amplitude is set by the modulation amplitude setting means and for calculating the concentration of interfering moisture present in the optical path space from the laser irradiation unit to the light reception unit excluding the sample cell based on the detection signal that is obtained when a relatively large modulation amplitude is set by the modulation amplitude setting means.

With the moisture measurement device according to the present invention, it is assumed that, even if the atmospheric condition within the sample cell may be a vacuum or at near-atmospheric pressure, the partial pressure of the water molecules is lower due to factors such as the gas to be measured being a gas with a low dew point. At the same time, it is assumed that the gas pressure of the space outside the sample cell, to be more specific, the gas pressure in the optical path space, excluding the sample cell, from the laser irradiation unit to the light reception unit is at substantially atmospheric pressure or higher than atmospheric pressure. Assuming that two types of modulation amplitude, a1 and a2 (where a2>a1), are used for the frequency modulation of laser light, the moisture detection sensitivity in an atmosphere at atmospheric pressure is higher when using a2, the larger amplitude, than a1. In contrast to this, in a vacuum atmosphere, especially in an atmosphere of high vacuum where the total pressure is no higher than 1 Torr, the moisture detection sensitivity is higher when using a1, the smaller modulation amplitude, than a2.

The moisture measurement device according to the present invention uses sensitivity difference that depends on modulation amplitude for a given gas pressure atmosphere so that a relatively small modulation amplitude is set for measuring moisture concentration in a gas to be measured having a vacuum atmosphere and a relatively large modulation amplitude is set for measuring the concentration of interfering moisture in a gas that is located outside the sample cell where the atmosphere is at substantially atmospheric pressure or higher. The modulation amplitude can be suitably set so long as the correct inequality relationship is maintained between a1 and a2, but to get a sufficient sensitivity difference, it is preferable to set a1 and a2 so that the following relationship is satisfied: a1 cm$^{-1}$<0.05<a2 cm$^{-1}$.

With the moisture measurement device according to the present invention, it is preferable to further include a control means that controls the modulation amplitude setting means and the moisture calculation means so that if the detection signal that is obtained when a relatively small modulation amplitude is set by the modulation amplitude setting means or the moisture concentration that is calculated based on said detection signal is less than a predetermined value, the modulation amplitude setting means sets a relatively large modulation amplitude so that the detection signal that is obtained under that condition is used as a basis for calculating the concentration of the interfering moisture.

The purpose of the moisture measurement device according to the present invention in most cases is to continuously monitor the moisture concentration in a gas to be measured. With respect to this, the afore-described configuration allows moisture concentration in a gas to be measured to be monitored substantially continuously. If the moisture concentration in a gas to be measured is so low that accurate measurement is not possible, the concentration of interfering moisture can be measured. This allows the concentration of the interfering moisture to be measured without impeding the monitoring of moisture concentration in a gas to be measured.

If the level of vacuum is high, even if the moisture concentration in a sample were to exceed a predetermined value, the detection signal that is obtained when a relatively large modulation amplitude is set and the detection signal that is obtained when a relatively small modulation amplitude is set can both be used. This allows the concentration of the interfering moisture to be roughly understood. This is because the sensitivity of detecting water molecules is affected less by differences in modulation amplitude in a vacuum atmosphere than in atmosphere at atmospheric pressure. This allows an approximate concentration of interfering moisture to be obtained by subtracting the moisture concentration obtained using a relatively small modulation amplitude from the moisture concentration obtained using a relatively large modulation amplitude.

One mode of a moisture measurement device according to the present invention is a configuration wherein one or a plurality of optical chambers featuring a sealed structure and housing said laser irradiation unit and said light reception unit are disposed in contact with said sample cell and also houses a dehumidifying drying means therewithin.

Here, a dehumidifying drying agent can be used as a dehumidifying drying means. It is more difficult with a dehumidifying drying agent to maintain a dehumidifying capacity as compared to, for example, purging by supplying a drying gas. However, with the moisture measurement device according to the present invention, because the concentration of interfering moisture can be monitored, any drop in dehumidifying capacity can be quickly detected, and appropriate measures can be implemented such as replacing the dehumidifying drying agent.

Furthermore, as one mode of the moisture measurement device according to the present invention, the afore-described sample cell can be a multiple-reflection type cell in which laser light is reflected a plurality of times by opposing wall surfaces. This extends the optical path length within the gas to be measured, meaning that even if the moisture quantity is low, the absorption of laser light is increased and the detection sensitivity is also increased. This increases the sensitivity and accuracy with which moisture concentration in a gas is measured.

Effects of the Invention

With the device for measuring moisture in a gas according to the present invention, the same measurement optical systems and circuits can be used to quickly and easily understand the effects of interfering moisture while measuring the target moisture concentration in a gas to be measured. This allows any inaccuracy in the measurements of moisture concentration in the gas to be measured or abnormalities of the dehumidifying system to be quickly notified to users. This allows, for example, the prevention of problems arising from supplying to a semiconductor manufacturing process a gas whose moisture concentration is higher than a prescribed level.

Furthermore, no additional overly complicated moving mechanisms or complicated control system circuits are required for monitoring the effects of the interfering moisture. The only thing required is to perform a measurement while changing the modulation amplitude of the laser light. This avoids large cost increases and also provides space saving advantages. Furthermore, since desiccants, which previously could not be used due to their easy susceptibility to performance changes, can be used within optical chambers for dehumidification, purging process based on the use of a dry gas is eliminated, thus reducing cost.

MODES FOR PRACTICING THE INVENTION

Figure 1:
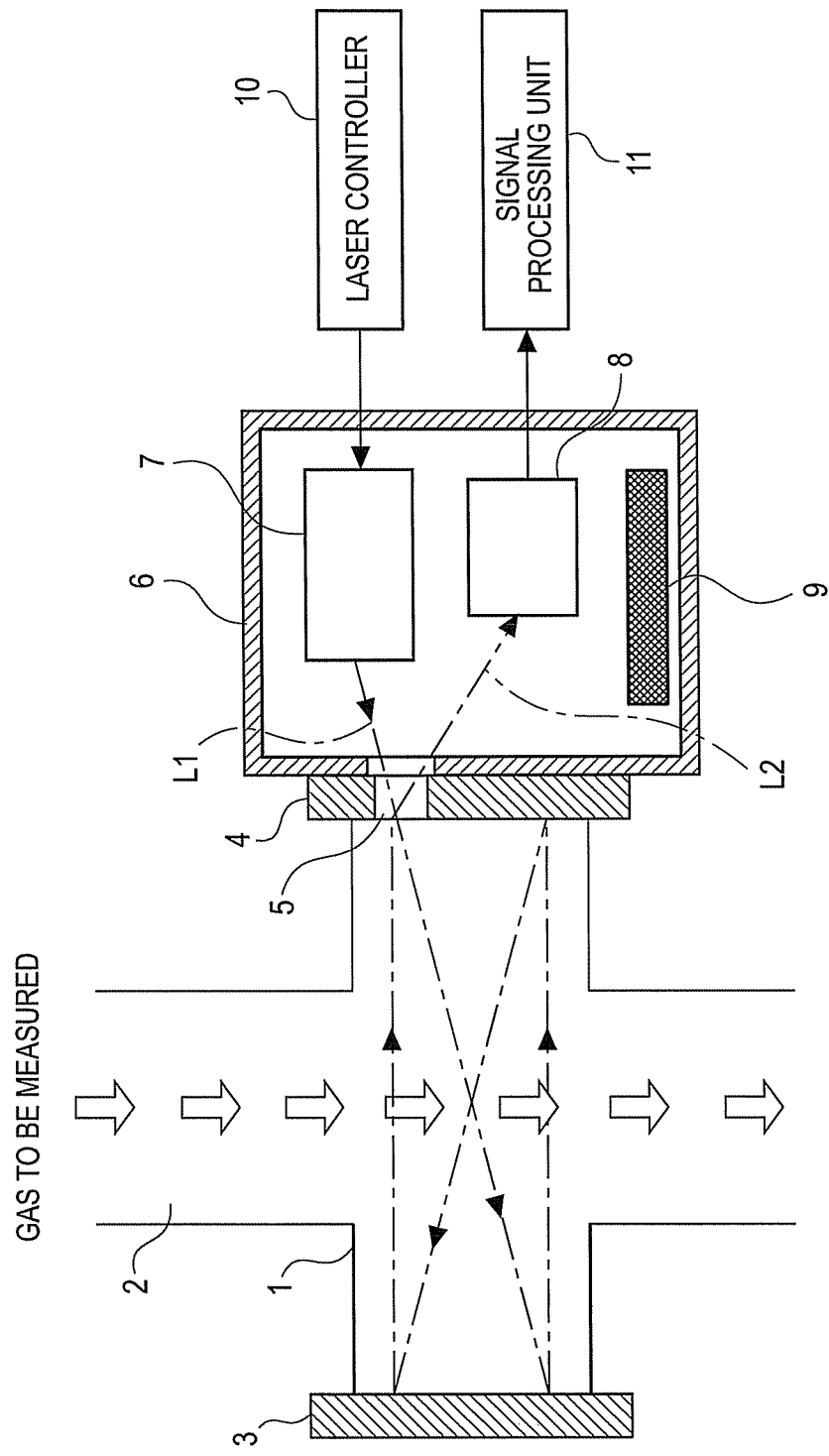
FIG. 1 shows a schematic view of the configuration of a measurement optical system in one embodiment of a moisture measurement device according to the present invention.
Figure 2:
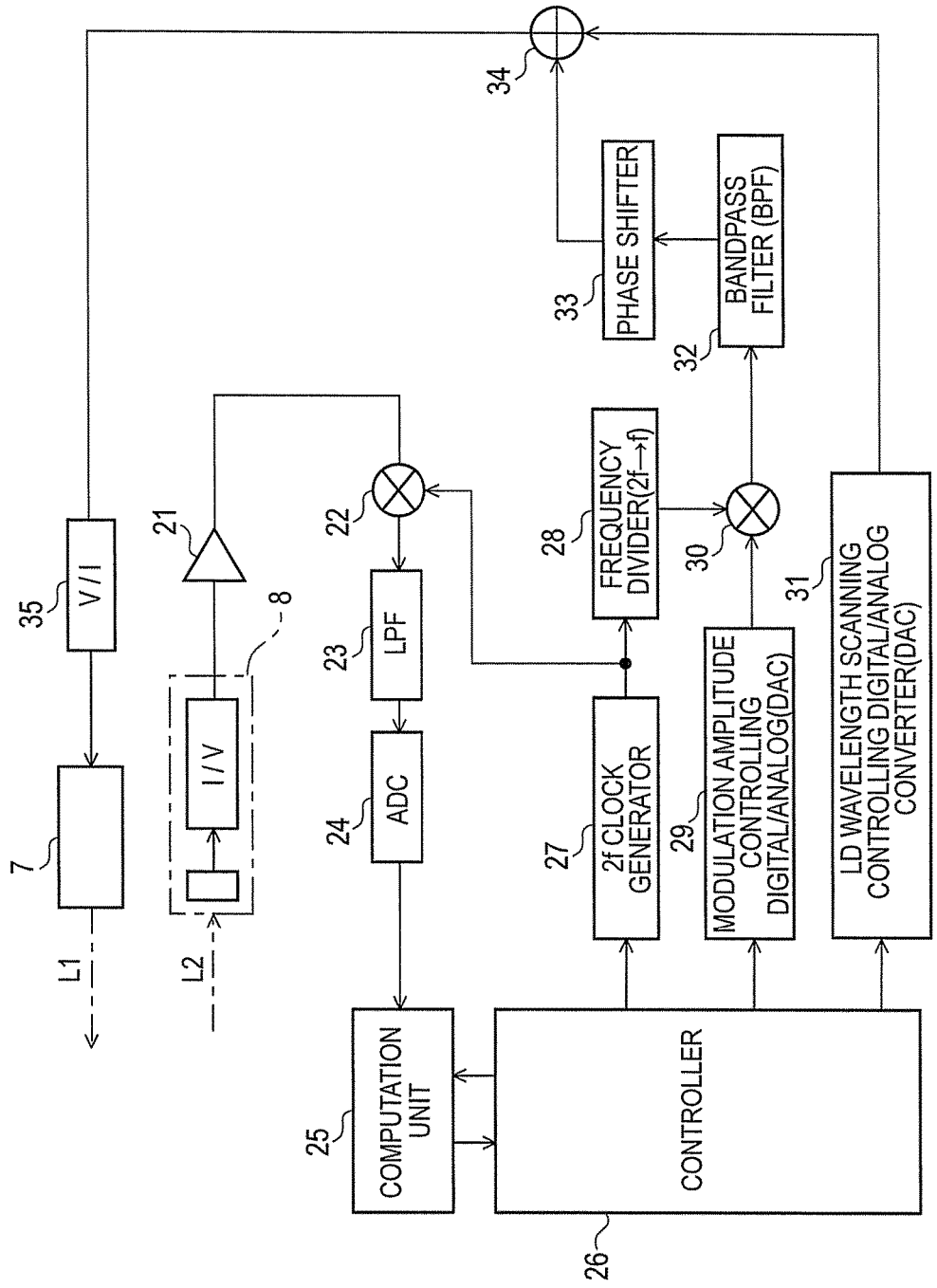
FIG. 2 shows a schematic view of the configuration of a signal processing system and a control system in the present embodiment of a moisture measurement device according to the present invention.

One embodiment of a moisture measurement device according to the present invention is described next with reference to the attached drawings. FIG. 1 shows a schematic view of the configuration of a measurement optical system in the present embodiment of the moisture measurement device. FIG. 2 shows a schematic view of the configuration of the signal processing system and the control system.

With the present embodiment of a moisture measurement instrument, a sample cell 1 that extends in a substantially horizontal direction is situated in a gas flow path 2 through which the gas to be measured flows in the top to bottom direction. Reflection mirrors 3 and 4 that oppose each other are disposed at the left and right open ends of sample cell 1. A transparent window 5 through which only light can pass is formed in one reflection mirror 3. Located on the outside of sample cell 1 with the transparent window 5 interposed in between is optical chamber 6 having a substantially sealed structure and its atmosphere at substantially atmospheric pressure. Disposed within said optical chamber 6 are wavelength-variable laser device 7 serving as a laser irradiation unit and photodetector 8 serving as a light reception unit. An example of a wavelength-variable laser device 7 is a DFB (distributed feedback) laser whose wavelength is in the near-infrared to mid-infrared region, but other laser devices can be used as well. The photodetector 8 includes a photoelectric conversion device 81 such as a photodiode and an I/V conversion amplifier 82 that converts a current signal obtained by the photoelectric conversion device to a voltage signal. With this example, a dehumidifying drying agent 9 is disposed within the optical chamber 6 for eliminating the interfering moisture. However, instead of the dehumidifying drying agent, a configuration can be used wherein a purge gas such as dry nitrogen is supplied into the optical chamber 6.

Laser light L1 that is emitted from wavelength-variable laser device 7 under the control of laser controller 10 passes through the transparent window 5 and enters the sample cell 1 and is repeatedly reflected by reflection mirrors 3 and 4. With the example of the optical path shown in FIG. 1, the laser light traverses across gas flow path 2 and makes two complete round-trips between reflection mirrors 3 and 4. However, the optical system can be constructed so that more complete round-trips are made. As the laser light travels through the gas flow path 2, the laser light is absorbed by various components that are included in the gas to be measured. The laser light L2 after the absorption by the various components passes through transparent window 5, returns to the optical chamber 6 and reaches the photodetector 8, which detects it and outputs an electrical signal that is input to signal processor 11. With the example shown in FIG. 1, the same transparent window 5 is used for both the emission from and incidence to sample cell 1 of the laser light. It is however also acceptable to provide separate transparent windows for the two purposes.

As shown in FIG. 2, the voltage signal that is obtained from photodetector 8 is amplified by amplifier 21 and is provided to synchronous detector 22. A clock signal with frequency 2f that is generated by a 2f clock generator 27, further described below, is input to the synchronous detector 22 as a reference signal. From the detection signal that is input to the synchronous detector 22 via the amplifier 21, the synchronous detector 22 extracts a signal that is in synchrony with the phase and frequency of the reference signal. Low-pass filter (LPF) 23 removes high-frequency components from the synchronized detection signal, which is then converted by an analog/digital converter (ADC) into a digital signal that is input to a computation unit 25.

Under the control of controller 26, the 2f clock generator 27 generates a clock signal with frequency 2f, and frequency divider 28 divides the frequency of the clock signal by two and generates a clock signal with frequency f and a duty ratio of 50%. The modulation amplitude controlling digital/analog converter (DAC) 29 converts the digital data provided by controller 26 to analog DC voltage values. The DC voltage and the clock signal with frequency f are multiplied by multiplier 30. The clock signal after the multiplication has an amplitude that is determined by the DC voltage. The band-pass filter (BPF) 32, which has a predetermined passband with center frequency f, converts a square-wave clock signal with center frequency f to a sine wave signal with center frequency f. The sine wave signal is used as the modulation signal for the frequency modulation.

The LD wavelength scanning digital/analog converter (DAC) 31 converts the digital data that is output by controller 26 for sweeping across a predetermined wavelength region close to the absorption spectrum of water molecules to an analog sweep voltage. The phase of the sine wave signal from the band-pass filter 32 is shifted by phase shifter 33 to be in synchrony with the detection signal. The sine wave signal is then added to the aforesaid sweep voltage by adder 34. The voltage with the modulation signal superimposed on the sweep voltage is converted to a current signal by voltage/current converter 35 and is supplied to wavelength-variable laser device 7 as a drive current. This causes the wavelength-variable laser device 7 to emit laser light L1 that is frequency modulated using a predetermined modulation amplitude and whose wavelength changes with passage of time. With this configuration, the modulation amplitude can be easily changed based on the data that is output from the controller 26 to the modulation amplitude controlling DAC 29.

Figure 4:
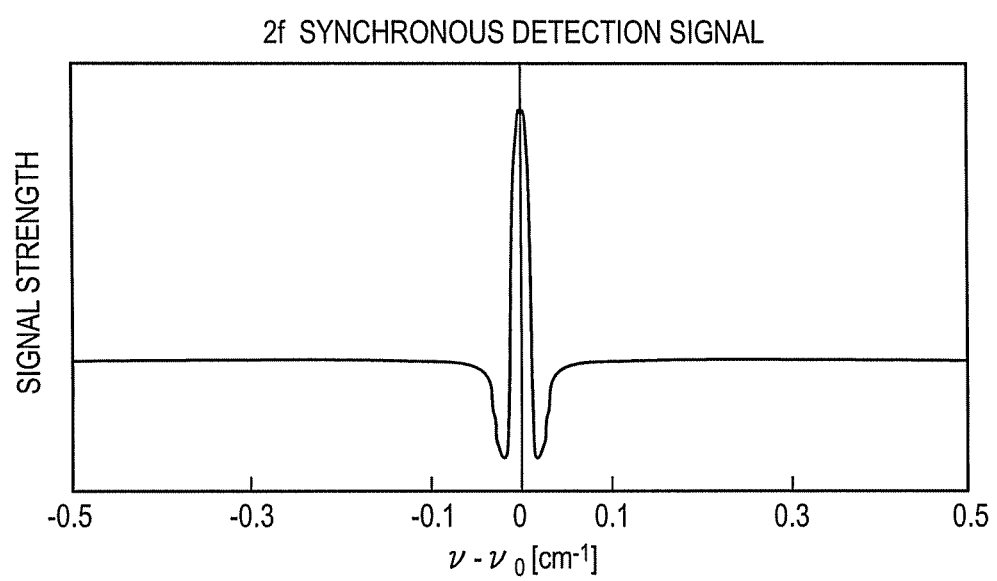
FIG. 4 shows one example of a 2f synchronized detection signal.

FIG. 4 shows an example of a 2f synchronized detection signal that is output from LPF 23. In FIG. 4, frequency deviation $v-v_0$ is plotted along the horizontal axis, and signal strength of the synchronized detection signal is plotted along the vertical axis. The signal strength at frequency deviation of zero, i.e., at center frequency $v_0$, indicates the magnitude of the absorption by the moisture, which can be used as the basis for calculating the moisture concentration.

In the configuration shown in FIG. 1, laser light that is emitted from wavelength-variable laser device 7 passes through the gas to be measured within sample cell 1 and the space within optical chamber 6 before reaching the photodetector 8. This means that the laser light is absorbed by not only the moisture that is included in the gas to be measured but also by the small amount of interfering moisture that is present in the space within the optical chamber 6. If the dehumidifying drying agent 9 is fully functioning, the amount of interfering moisture will be very small, and its effect on the calculated moisture concentration in the gas to be measured will be minimal. However, if the moisture concentration in the space within the optical chamber 6 increases due to factors such as the reduced efficacy of the dehumidifying drying agent 9, the accuracy of the calculated moisture concentration in the gas to be measured will decrease. For this reason, the present moisture measurement device performs the following characteristic operations to suitably monitor the moisture concentration within optical chamber 6.

First, the relationship between the sensitivity of moisture detection and different modulation amplitudes used in the frequency modulation of laser light is described with reference to one example of a measurement. In this example, the length of the optical path within sample cell 1 is 200 cm, the length of the optical path in the space within the optical chamber 6 is 20 cm, the total pressure of the gas to be measured is 0.1 Torr, the total pressure within optical chamber 6 is 760 Torr, the partial pressure of the interfering moisture in optical chamber 6 is 50 ppm, and the center wavelength of the laser light is approximately 1.3 µm.

Figure 5:
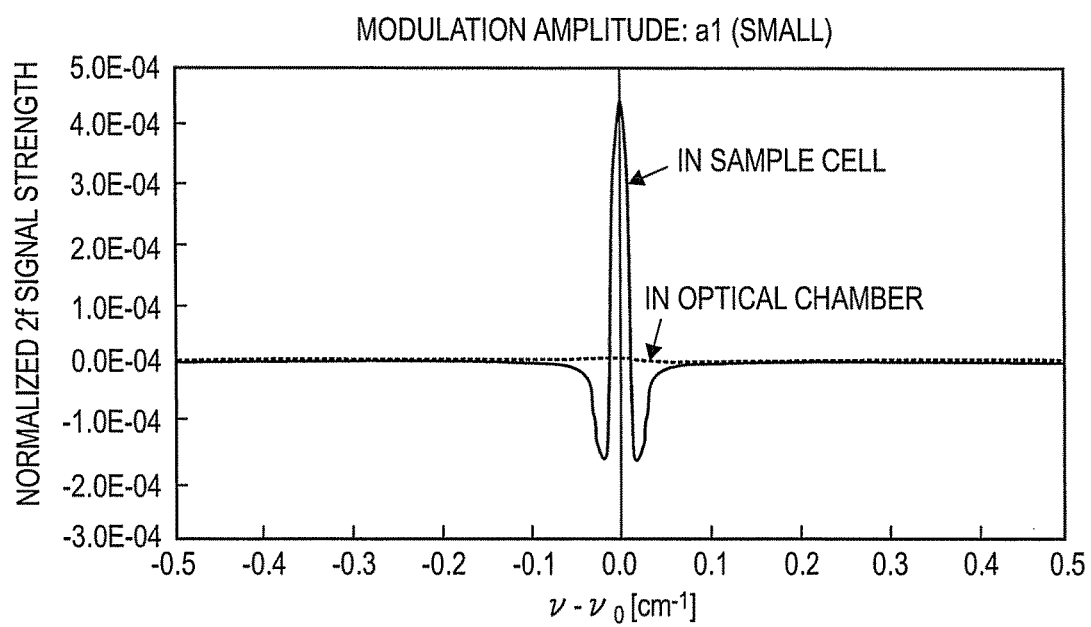
FIG. 5 shows the calculated result of secondary harmonic synchronous detection signals for moisture within the sample cell and moisture within the optical chamber.

FIG. 5 shows the results of the calculation (simulation) of secondary harmonic synchronous detection signals for moisture in sample cell 1 and moisture in optical chamber 6 for modulation amplitude a1=0.01 cm$^{-1}$ and the partial pressure of moisture in sample cell 1 of 0.5 mTorr. The synchronized detection signal that is obtained with an actual device will be the sum of the two secondary harmonic synchronous detection signals shown in FIG. 5, and separating the two computationally is difficult. (The same also applies to FIG. 6 and FIG. 7.) With the condition shown in FIG. 5, because the strength of the secondary harmonic synchronous detection signal for the moisture in sample cell 1 is much larger relative to the moisture in the optical chamber 6, the effects of the interfering moisture in the optical chamber 6 can be ignored. Stated otherwise, the result of the moisture concentration that is calculated by computation unit 25 based on the synchronized detection signal can be deemed as representing the moisture concentration in sample cell 1.

Figure 6:
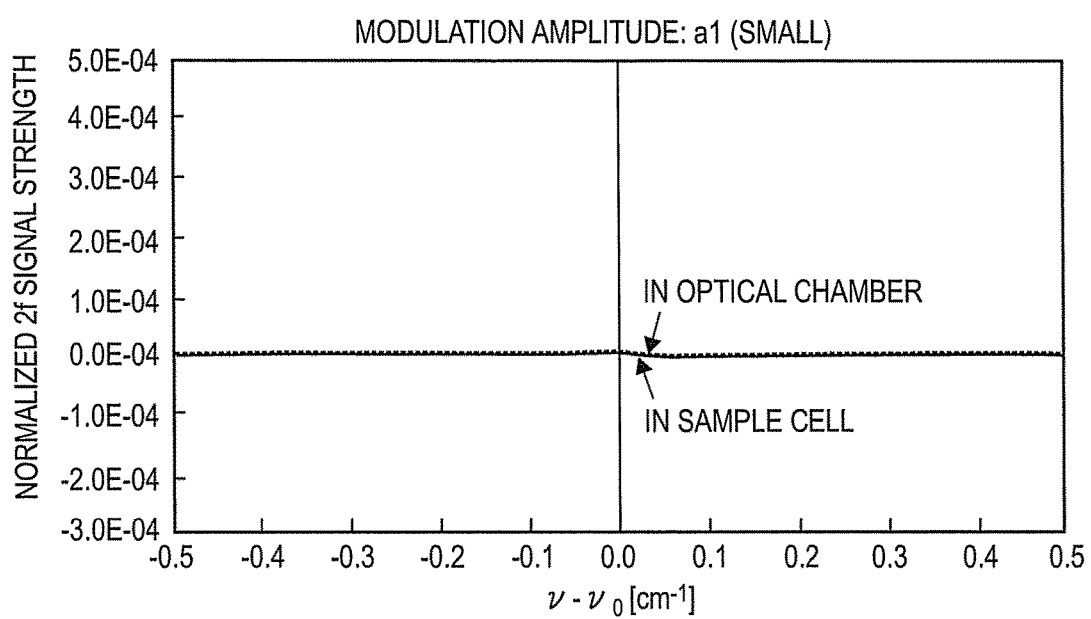
FIG. 6 shows the calculated result of secondary harmonic synchronous detection signals for moisture within the sample cell and moisture within the optical chamber.

FIG. 6 shows the calculated secondary harmonic synchronous detection signals for moisture in sample cell 1 and moisture in optical chamber 6 for modulation amplitude a1=0.01 cm$^{-1}$ and the partial pressure of moisture in sample cell 1 of 0.001 mTorr. In this case, because the amount of moisture in sample cell 1 is small and the amount of absorption of laser light is small, the signal strength is much less. In fact, if the signal strength is only about this level, it is difficult to accurately calculate the moisture concentration.

Figure 7:
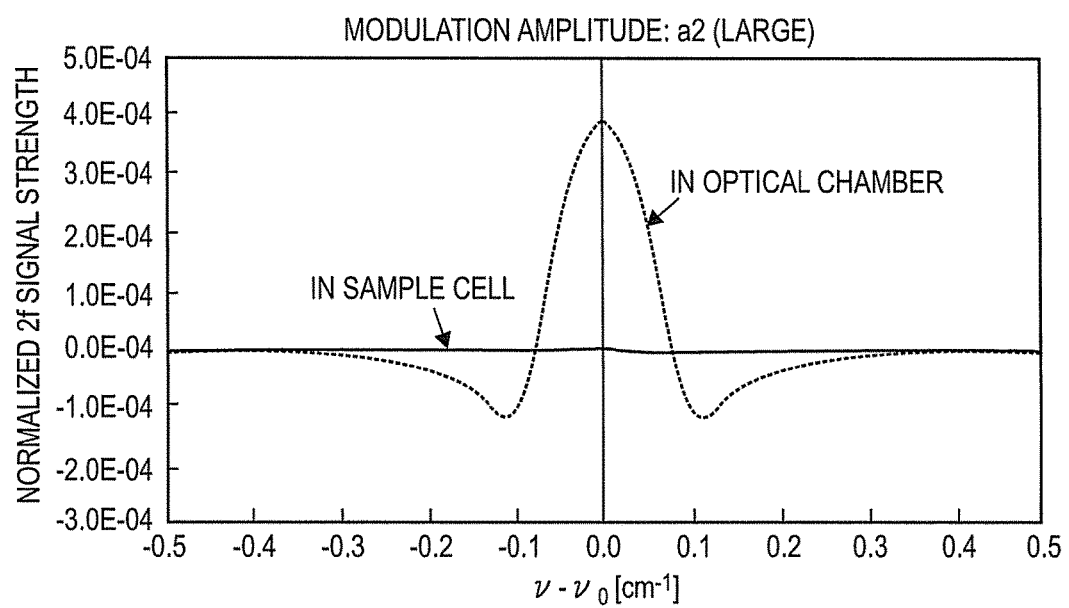
FIG. 7 shows the calculated result of secondary harmonic synchronous detection signals for moisture within the sample cell and moisture within the optical chamber.

FIG. 7 shows the secondary harmonic synchronous detection signals for moisture in sample cell 1 and moisture in optical chamber 6 for partial pressure of moisture in sample cell 1 of 0.001 mTorr, the same as for FIG. 6, but using a modulation amplitude of a2=0.1 cm$^{-1}$ instead. In this case, even though the signal strength for moisture in sample cell 1 is substantially the same as that shown in FIG. 6, the signal strength for moisture in optical chamber 6 is extremely large. The signal strength for moisture in sample cell 1 is so low to be almost negligible. In other words, by simply changing the modulation amplitude from a1 to a2, the moisture concentration in the optical chamber 6 has become detectable.

Shown below are preferable conditions for detecting moisture in the space in optical chamber 6 with a high accuracy based on the synchronized detection signal.
Condition 1: Modulation amplitude a1 be such that a1 cm$^{-1}$≤2.2×$\gamma_{ED}$ when measuring the gas to be measured.
Condition 2: Moisture concentration in the gas to be measured under condition 1 be less than the detectable limit of the device.
Condition 3: Modulation amplitude a2 be such that a2 cm$^{-1}$≥10×a1 when measuring moisture in optical chamber 6. However, these are not indispensable conditions. In particular, with Condition 1 and Condition 3, if the relationship a1<a2 is satisfied and if the relationship a1 cm$^{-1}$<0.05<a2 cm$^{-1}$ is satisfied, there will be enough sensitivity difference at the respective modulation amplitudes.

Figure 3:
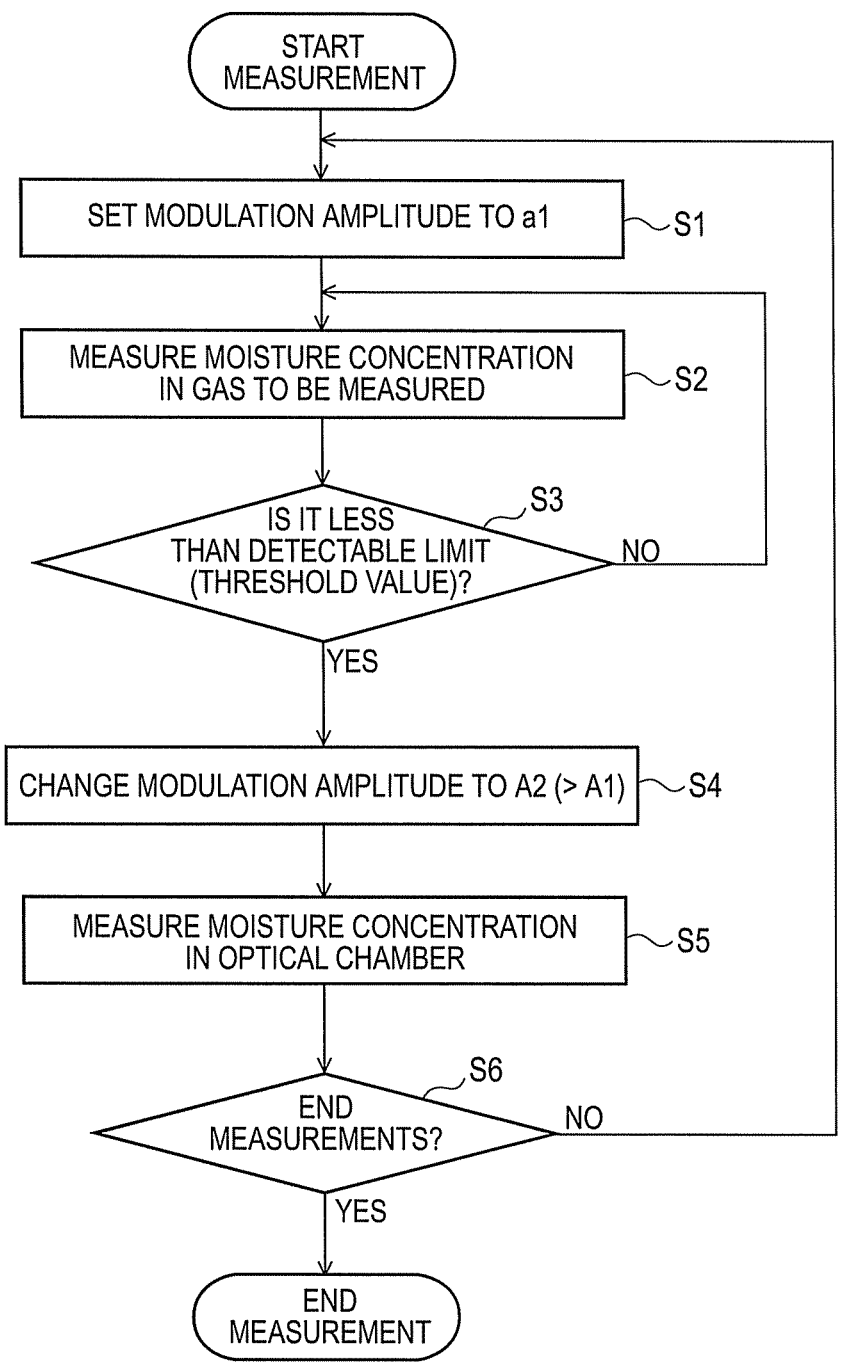
FIG. 3 shows a flowchart of the measurement operation in the present embodiment of a moisture measurement device.

FIG. 3 shows one example of the flowchart of the measurement operation of the moisture measurement device according to the present embodiment. Once the measurement is started, controller 26 sets the modulation amplitude to a1 (=0.01 cm$^{-1}$) (step S1). To explain, the data corresponding to modulation amplitude a1 is output to modulation amplitude controlling DAC 29 and the measurement is performed according to the afore-described operation (step S2). This means that the wavelength is swept over a predetermined range, and laser light L1 that is frequency modulated using modulation amplitude a1 is emitted from wavelength-variable laser device 7. The laser light L2 that has passed through and has been absorbed by the gas to be measured in sample cell 1 is detected by photodetector 8. The resulting secondary harmonic synchronous detection signal is processed by computation unit 25, and the moisture concentration is calculated. The moisture concentration that is obtained can be deemed as representing the moisture concentration of the gas to be measured in sample cell 1.

If, for example, a high vacuum is created within sample cell 1 and the pressure becomes no more than 1 Torr and the partial pressure of the water molecules becomes very low, or if a gas with a low dew point is introduced into gas flow path 2 despite the atmosphere being at substantially atmospheric pressure, the absorbance by water in sample cell 1 will drop dramatically, and afore-mentioned Condition 2 will be satisfied. To explain, if the computation unit 25 determines that the signal strength of the synchronized detection signal has dropped below a threshold value and is below the detectable limit ("YES" in step S3), controller 26 changes the modulation amplitude to a2 (=0.1 cm$^{-1}$) (step S4). In other words, controller 26 outputs a data corresponding to modulation amplitude a2 to modulation amplitude controlling DAC 29, and the measurement is performed according to the afore-described operations (step S5).

As afore-described, because the synchronized detection signal that is obtained will be a sum of the two signals shown in FIG. 7, the moisture concentration that is calculated by computation unit 25 based on the synchronized detection signal can be deemed as representing the moisture concentration in the space within optical chamber 6. The controller then decides whether or not an instruction has been issued to stop the measurements (step S6), and if termination of measurements has not been instructed, the process returns to step S1 and measurements are continued.

This allows the moisture concentration in the space within optical chamber 6 to be calculated with a high accuracy when the moisture concentration in the gas to be measured is low. The results of these calculations so obtained are displayed on a display not illustrated and allows visual confirmation by, for example, the operator. Alternatively, an upper limit can be set for moisture concentration in the space in the optical chamber 6 so that an abnormality notice is issued if the upper limit is exceeded. By so doing, if the moisture concentration within optical chamber 6 becomes abnormally high, the operator is immediately notified for an appropriate response.

Figure 8:
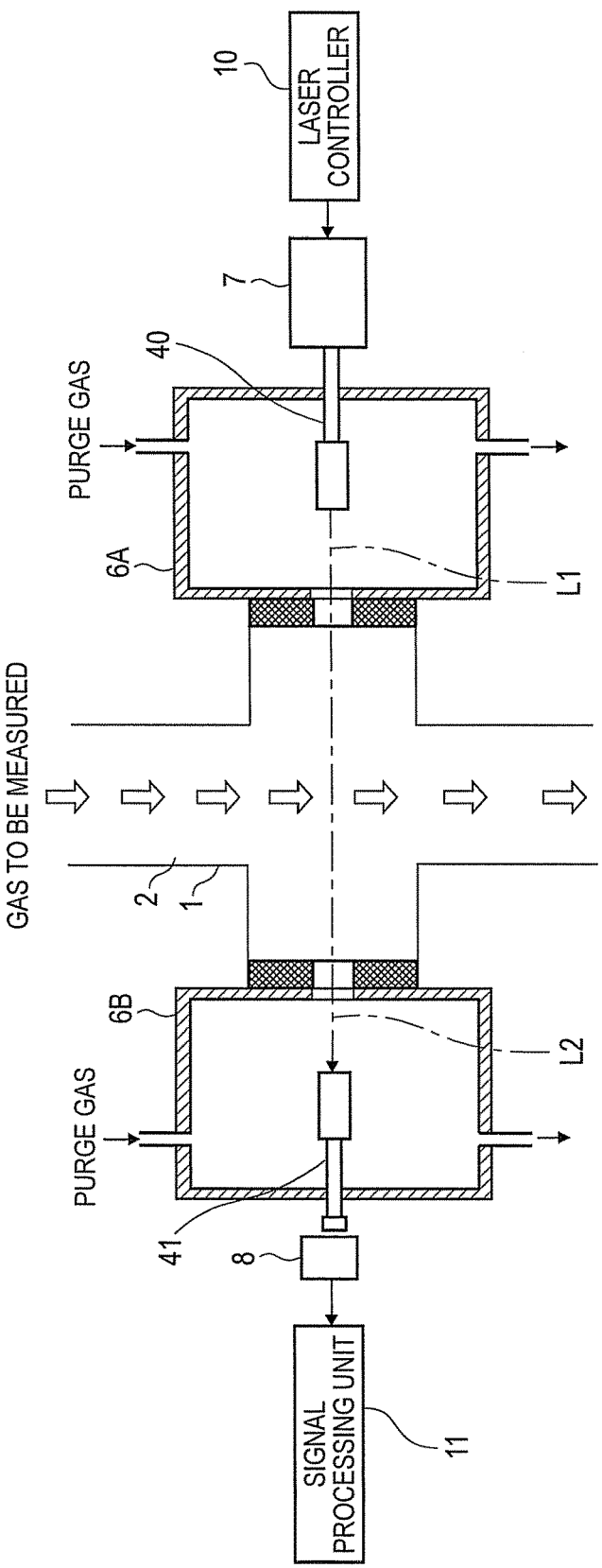
FIG. 8 shows a schematic view of the configuration of a measurement optical system in another embodiment of a moisture measurement device according to the present invention.

FIG. 8 shows a schematic view of the configuration of a measurement optical system in another embodiment of a moisture measurement device according to the present invention. The same numerical references are used for the same components as in the afore-described embodiment, and their description is omitted here. In the configuration of this embodiment, optical chambers 6A and 6B are disposed at either end of a sample cell 1. Laser light that is emitted by a wavelength-variable laser device 7 that is disposed outside optical chamber 6A is led by an optical guide path 40 such as an optical fiber into optical chamber 6A where the laser light is emitted from the end of the optical guide path 40 to irradiate into sample cell 1. Another optical guide path 41 is disposed within the other optical chamber 6B to guide the laser light to a photodetector 8 that is disposed outside the optical chamber 6B. The laser light L2 that has passed through sample cell 1 becomes incident to the end of the optical guide path 41. A dry gas serving as a purge gas can be continuously supplied into optical chambers 6A and 6B, but it is also possible as in the earlier described embodiment to internally house a dehumidifying drying agent.

Even though the configuration of the measurement optical system may differ as in the case here, the signal processing system and the control system are absolutely identical, and the measurement operations used for calculating the moisture concentration in the space within optical chambers 6A and 6B are also the same. Also, an optical guide path can be used to guide the laser light into and out from the measurement optical system shown in FIG. 1.

Furthermore, the afore-described embodiments are just examples of the present invention, and modifications, additions, changes and the like can be made to matters not described above within the gist of the present invention and still be included within the claims of the present invention.

DESCRIPTION OF THE NUMERICAL REFERENCES

1. Sample cell
2. Gas flow path
3, 4. Reflection mirror
5. Transparent window
6. Optical chamber
7. Wavelength-variable laser device
8. Photodetector
81. Photoelectric conversion device
82. I/V conversion amplifier
9. Dehumidifying drying agent
10. Laser controller
11. Signal processing unit
21. Amplifier
22. Synchronous detector
23. Low-pass filter
24. Analog/digital converter
25. Computation unit
26. Controller
27. 2f clock generator
28. Frequency divider
29. Modulation amplitude controlling digital/analog converter
30. Multiplier
31. LD wavelength scanning controlling digital/analog converter
32. Band-pass filter
33. Phase shifter
34. Adder
35. Voltage/current converter
40, 41. Optical guide path

What is claimed is:

1. A device for measuring moisture in a gas, said device comprising:
   a sample cell where gas to be measured is introduced;
   a laser irradiation unit and a light reception unit disposed outside of said sample cell;
   wherein said laser irradiation unit is configured to modulate light using frequency f and said light reception unit detects light after passing through the gas to be measured in said sample cell;
   the detected signal by the light reception unit is synchronously detected using a frequency that is an integer-multiple of frequency f; and
   concentration of moisture that is included in said gas to be measured is calculated based on the detected signal;
   a modulation amplitude setting means for switchably setting the modulation amplitude between at least two types; and
   a moisture calculation means for calculating moisture concentration in said sample cell based on detection signal that is obtained when a relatively small modulation amplitude is set by said modulation amplitude setting means and for calculating the concentration of interfering moisture present in the optical path space, excluding said sample cell, from said laser irradiation unit to said light reception unit based on the detection signal that is obtained when a relatively large modulation amplitude is set by said modulation amplitude setting means.

2. The device for measuring moisture in a gas according to claim 1 further comprising a control means for controlling said modulation amplitude setting means and said moisture calculation means so that if the detection signal that is obtained when a relatively small modulation amplitude is set by said modulation amplitude setting means or the moisture concentration that is calculated based on said detection signal is less than a predetermined value, said modulation amplitude setting means sets a relatively large modulation amplitude so that the detection signal that is obtained under that condition is used as a basis for calculating the concentration of interfering moisture.

3. The device for measuring moisture in a gas according to claim 1 further comprising a control means for controlling said modulation amplitude setting means and said moisture calculation means so that the concentration of interfering moisture is measured under a condition of high vacuum where the total pressure of the gas to be measured in the sample cell is no more than 1 Torr.

4. The device for measuring moisture in a gas according to claim 1 wherein one or a plurality of optical chambers featuring a sealed structure and housing said laser irradiation unit and said light reception unit are disposed in contact with said sample cell and also houses a dehumidifying drying means therewithin.

5. The device for measuring moisture in a gas according to claim 1 wherein said sample cell is a multiple-reflection type cell in which laser light is reflected a plurality of times by opposing wall surfaces.

6. A device for measuring moisture in a gas, said device comprising:
   a sample cell where gas to be measured is introduced;
   a laser irradiation unit and a light reception unit disposed outside of said sample cell;
   wherein said laser irradiation unit is configured to modulate light using frequency f and said light reception unit detects light after passing through the gas to be measured in said sample cell;
   the detected signal by the light reception unit is synchronously detected using a frequency that is an integer-multiple of frequency f; and
   concentration of moisture that is included in said gas to be measured is calculated based on the detected signal;
   a modulation amplitude setting means for switchably setting the modulation amplitude between at least two types; and
   a moisture calculation means for calculating moisture concentration in said sample cell based on detection signal that is obtained when a relatively small modulation amplitude is set by said modulation amplitude setting means and for calculating the concentration of interfering moisture present in the optical path space, excluding said sample cell, from said laser irradiation unit to said light reception unit based on the detection signal that is obtained when a relatively large modulation amplitude is set by said modulation amplitude setting means, wherein two types of modulation amplitudes, a1 and a2, that are set by said modulation amplitude setting means satisfy the relationship a1 $cm^{-1}$<0.05<a2 $cm^{-1}$.

7. A device for measuring moisture in a gas, said device comprising:
 a sample cell where gas to be measured is introduced;
 a laser irradiation unit and a light reception unit disposed outside of said sample cell;
 wherein said laser irradiation unit is configured to modulate light using frequency f and said light reception unit detects light after passing through the gas to be measured in said sample cell;
 the detected signal by the light reception unit is synchronously detected using a frequency that is an integer-multiple of frequency f; and
 concentration of moisture that is included in said gas to be measured is calculated based on the detected signal;
 a modulation amplitude setting means for switchably setting the modulation amplitude between at least two types;
 a moisture calculation means for calculating moisture concentration in said sample cell based on detection signal that is obtained when a relatively small modulation amplitude is set by said modulation amplitude setting means and for calculating the concentration of interfering moisture present in the optical path space, excluding said sample cell, from said laser irradiation unit to said light reception unit based on the detection signal that is obtained when a relatively large modulation amplitude is set by said modulation amplitude setting means; and a control means for controlling said modulation amplitude setting means and said moisture calculation means so that if the detection signal that is obtained when a relatively small modulation amplitude is set by said modulation amplitude setting means or the moisture concentration that is calculated based on said detection signal is less than a predetermined value, said modulation amplitude setting means sets a relatively large modulation amplitude so that the detection signal that is obtained under that condition is used as a basis for calculating the concentration of interfering moisture, wherein two types of modulation amplitudes, a1 and a2, that are set by said modulation amplitude setting means satisfy the relationship a1 $cm^{-1}$<0.05<a2 $cm^{-1}$.

* * * * *